United States Patent [19]

Hatcher

[11] Patent Number: 4,996,053
[45] Date of Patent: Feb. 26, 1991

[54] BAIT FOR CONTROLLING DARKLING BEETLES, LESSER METAL WORMS AND HIDE BEETLES

[76] Inventor: Richard P. Hatcher, P.O. Box 60, Watkinsville, Ga. 30677

[21] Appl. No.: 440,200

[22] Filed: Nov. 22, 1989

[51] Int. Cl.⁵ ............................................. A01N 25/08
[52] U.S. Cl. .................................... 424/410; 424/405; 424/409; 424/407; 424/659; 426/1
[58] Field of Search ............... 424/405, 408, 409, 410, 424/84, 657, 658, 659; 426/1

[56] References Cited

U.S. PATENT DOCUMENTS

| | | | |
|---|---|---|---|
| 2,811,479 | 10/1957 | Geary | 424/410 |
| 3,937,826 | 2/1976 | Harris | 424/410 |
| 4,321,258 | 3/1982 | Dunlap | 514/770 |
| 4,461,758 | 7/1984 | Brite | 424/10 |
| 4,581,378 | 4/1986 | Lazar et al. | 424/410 |
| 4,759,930 | 7/1988 | Graniver et al. | 424/659 |
| 4,826,682 | 5/1989 | Sakharova | 424/659 |
| 4,889,710 | 12/1989 | Hagarty | 424/45 |
| 4,944,950 | 7/1990 | Sakharova | 424/659 |

FOREIGN PATENT DOCUMENTS

| | | | |
|---|---|---|---|
| 7223198 | 6/1972 | Japan | 424/84 |
| 0290188 | 7/1953 | Switzerland | 424/658 |

*Primary Examiner*—Thurman K. Page
*Assistant Examiner*—James M. Spear
*Attorney, Agent, or Firm*—Michael V. Drew

[57] ABSTRACT

An insecticidal bait comprises about 55.5% to about 75.5% by weight of a ground cereal grain; from about 20% to about 40% by weight of powdered boric acid, from about 1% to about 5% by weight of an edible oil from the class consisting of corn oil and soy oil, and from about 1% to about 5% by weight of silica gel. From about 0.05% to about 0.2% of a non-white coloring agent may also be added.

16 Claims, No Drawings

BAIT FOR CONTROLLING DARKLING BEETLES, LESSER METAL WORMS AND HIDE BEETLES

TECHNICAL FIELD OF THE INVENTION

This invention relates to insecticidal baits, and more particularly to insectidical baits for darkling beetles, lesser meal worms, and hide beetles.

BACKGROUND OF THE INVENTION

Darkling beetles and hide beetles are two of several insects which infest poultry houses. Darkling beetles and hide beetles are members of the taxonomical Order Coleoptera. Darkling beetles are classified under the Family Tenebrionidae. Darkling beetle is the common name for the species classified as *Alphitobius diaperinus*. The term darkling beetle is commonly used to refer to the species in the adult stage while "lesser meal worm" is used to refer to the species in the larval stage. Hide beetles are classified under the family Dermestidae. Hide beetle is the common name for the species *Dermestes maculatus*. These insects, darkling beetles, lesser meal worms and hide beetles, are pests which are not desired in poultry houses because they (1) consume significant quantities of food which is set out for poultry, (2) destroy components of the poultry house, and (3) transmit infectious disease agents within poultry houses, among adjacent poultry houses, and in nearby dwellings. In addition, darkling beetles are known to serve as intermediate hosts for certain undesirable parasites.

Darkling beetles, lesser meal worms and hide beetles, are extremely prolific. Upon the infestation of a poultry house by relatively few of these insects, their numbers can extend into the millions within a few weeks if they are not controlled.

The darkling beetle, lesser meal worm and hide beetle invade and consume significant quantities of poultry feed. For example, a poultry house with 20,000 broiler chickens may be moderately infested by about 4 million beetles. During a typical 50-day grow-out period (i.e., the growth cycle for the fowl) these beetles can consume 400 pounds of poultry feed. This problem causes the poultry owner to incur additional expense to replace feed consumed by the insects.

Darkling beetles, lesser meal worms and hide beetles also destroy components of poultry houses by eating through or burrowing through insulation, side wall curtains, electrical insulation, and wood. These components must be replaced or repaired, requiring the poultry house owner to incur additional operating expenses. If damage is sufficiently severe, it may not be possible to use the structure until repairs are completed.

The insects are known to transmit infectious disease agents such as *Escherichia coli*, Salmonella, Clostridium, Mareks disease virus, laryngotrachaetitis virus, and infectious bursal disease virus. These disease agents carried by the insects are harmful to poultry and humans.

Darkling beetles are known to serve as intermediate hosts in the life cycle of cecal worms and avian tapeworms. These two internal parasites are very harmful to poultry.

Fowl are very densely housed in facilities to maximize the operator's resources. Because the houses are so densely populated, any diseases or viruses which infect one or a small number of fowl will quickly spread to other unaffected fowl. The same is true for the spread of parasites.

For the reasons stated above, it is extremely important that poultry houses be kept free of darkling beetles, lesser meal worms, and hide beetles, and that any infestation by them be curtailed or controlled as quickly as possible. The larval stage of the darkling beetle, i.e., the lesser meal worm, is mentioned singly because it is very destructive in this stage of growth. The lesser meal worm is at least as destructive as the adult darkling beetle. It is important to control the lesser meal worm because the beetle stays in that larval maturation phase for 3 to 7 weeks. The meal worm can do substantial damage during that period. In addition, since the adult darkling beetle can live in a poultry house for up to two years, it is important that they be prevented from reaching the adult stage, if possible.

It is known that insects are generally attracted to their food source. For this reason, a method of killing certain insects consists of combining a food source for the insects with a substance which is toxic to them or otherwise adversely affects them. The mixture is commonly referred to as "bait." The bait is made accessible to the insect. The insect is normally attracted to the bait and either consumes the food source which is laced with the toxic substance or is adversely affected by other ingredients. For killing by consumption, optimally, enough of the toxic substance is consumed to immediately or ultimately kill the insect. Some baits employ a toxicant which adversely affects the insect by topical contact. Some employ a substance which is not poisonous but which so adversely affects the insect that it is rendered ineffective, incapacitated, or mortally affected. Insect baits in general are well known in the art.

Boron-containing substances are known insect toxicants. In particular, boric acid has been used.

Insect baits in general and baits and pesticides which employ boric acid are disclosed in the following U.S. patents and foreign patents:

| Inventor | Patent Number | Year of Issue |
| --- | --- | --- |
| Susuki | 4,657,912 | 1987 |
| Brite | 4,461,758 | 1984 |
| Dunlap | 4,321,258 | 1982 |
| Balsley | 4,320,130 | 1982 |
| Geiger | 3,470,293 | 1969 |

| Country | Patent Number | Year of Issue |
| --- | --- | --- |
| U.K. | 2,070,430 | 1981 |
| Canada | 1,112,158 | 1981 |
| Canada | 1,093,961 | 1981 |
| Canada | 978,853 | 1975 |
| Belgium | 755,598 | 1971 |
| Italy | 301,094 | 1932 |
| France | 714,413 | 1931 |
| Japan | J6 1,078,705 | 1986 |
| Japan | J5 9,128,317 | 1983 |

SUMMARY OF THE INVENTION

It is an object of the invention to provide an insecticide bait which is highly effective in controlling darkling beetles, lesser meal worms and hide beetles.

It is a further object of the invention to provide a bait which achieves a highly effective kill ratio.

The invention attains the above objects by providing an insecticide bait comprising ground cereal grain as a food source, a boron-containing substance as the toxicant, an edible oil such as corn oil or soy oil, silica gel as a synergist, and pigment.

DESCRIPTION OF PREFERRED EMBODIMENTS OF THE INVENTION

The composition according to the present invention can best be characterized by first defining the effective mechanism by which the composition operates. It is known in the art that boron is an effective insecticide for darkling beetles, lesser meal worms and hide beetles. However, the boron acts best as an insecticide if the insects actually consume the boron rather than merely being exposed to the boron by casual contact. Consumption of the toxicant by the insects is insured by mixing it with edible food for the insects. Edible foods for darkling beetles, lesser meal worms and hide beetles include ground cereal grains. Cereal grains include grains from corn, wheat, rice, and sorghum. Experimentation in the development of the invention revealed that wheat middlings and corn meal in particular are inexpensive edible foods which work well with the invention. The insects (darkling beetles, lesser meal worms and hide beetles) are attracted to these edible foods and will eat them along with other components of the herein described composition.

Examples of boron substances are disodium octaborate tetrahydrate and boric acid. Experimentation in the development of the invention revealed that powdered boric acid is a preferred boron substance which works well in the mixture of the invention.

The combination of an edible food with various insecticides has been previously disclosed in the art as a means to insure attraction of insects to the active ingredient. The concept used in the present invention is to employ the edible food primarily as a means to insure consumption of the active ingredient rather than for the edible food to serve as an attractant.

The ratio between the edible food (the "bait" component) and the toxicant is critical for reasons of both cost and efficacy, with the latter being more critical. If the concentration of toxicant in the bait composition is too small, too few beetles will be killed to be significant. If the concentration of toxicant is too great, the beetles will not consume enough (and in some instances not any) of the composition, and too few beetles will be killed to be significant. It is desirable that the concentration of the boron substance in the composition be kept at a minimum to preserve the ecological balance in the disposal area upon disposal of the composition after use. The reason is that when the poultry house is cleaned out, the bait is removed along with fowl droppings and other material from the floor of the poultry house. The removed material is normally deposited somewhere outdoors. Often it is used as fertilizer. The boron which is present in the composition does not degrade. Although boron is present in the environment, an increased accumulation of boron could upset the ecological balance. The present invention defines an optimum ratio of ingredients that will result in a maximum kill of darkling beetles, lesser meal worms and hide beetles in a minimum period of time, with the lowest concentration of boron. The optimum percentages by weight for the composition were found to be about 55.5% to about 75.5% of wheat middlings or corn meal, and about 20% to about 40% of powdered boric acid. Preferable percentages by weight are 65.5% of ground grain and 30% of powdered boric acid.

Experimentation in formulating the invention composition revealed that the addition of other ingredients increased the efficacy of the mixture. Edible oils were discovered to increase the effectiveness of the mixture. The edible oil, preferably corn oil or soy oil, creates two benefits:

(1) the oil is an additional food source for the beetles, and (2) the oil makes the grain food source sticky on its outer surface, which makes the other ingredients of the mixture adhere to and mix more securely with the grain food base.

It is important that the oil be added in an optimum quantity. The addition of greater than 5.0% by weight of oil made the mixture too oily, resulting in difficulties in obtaining a uniform mixture of components in the bait. Addition of less than 1.0% by weight results in ineffective adherence between the grain and other elements. The preferred percentage of oil is 2.5%.

Experimentation with various components also revealed that the addition of silica gel greatly increased the efficacy of the composition. It was determined that the silica gel has a synergistic effect with the other components, resulting in the killing of a greater number of beetles. Silica gel and other forms of silica have been previously disclosed as additives to various insecticidal preparations. However, the addition of this component has been as an "anticaking" agent or to alter the physical appearance of the preparation. (See patent references cited above) It is disclosed in the present invention that silica gel acts as a synergist with a boron containing substance when used as an insecticide for darkling beetles, lesser meal worms and hide beetles. Brands of silica gel which work well in the composition are Sipernat 22 and Wessalon 22. The optimal percentage by weight of silica gel is from about 1% to about 5%. Preferably, 2% is used.

A non-white pigment may be added to the composition for two purposes: (A) To distinguish the composition from other items such as food or feed. (B) To provide a means for monitoring (i) the consumption of the composition by the beetles and (ii) subsequent travel of the beetles after consumption of the composition. This means for monitoring occurs because the coloring (pigment) shows up in droppings from the beetles. Dayglo Aurora Pink pigment is a brand of pigment which is particularly useful because its presence is readily detectable when exposed to ultra-violet (UV) light.

The composition is essentially dry and is not obnoxious or dangerous to humans or poultry. It may be spread by hand or via fertilizer spreader. It may be broadcast in a poultry house or other enclosure in an area infested or inhabited by darkling beetles, lesser meal worms and hide beetles, or in an area that is expected to become inhabited by them.

It was discovered during experimentation that the composition mixes more thoroughly and is more efficacious when the ingredients are mixed in a particular order. To ensure maximum adherence of the toxicant (powdered boric acid) and the synergist (silica gel) to the primary edible food substance (ground grain, i.e., wheat middlings or corn meal), the primary edible food substance is first mixed thoroughly with the edible oil. The silica gel is then blended into the mixture. Since the concentration of silica in this invention is less than that of the boron-containing substance, the silica must be added before the boron-containing substance. Otherwise, the boron-containing substance could saturate the adherence properties of the edible-food/boron-containing-substance mixture and prevent appropriate adherence of the silica to the edible food. This mixture of three components is thoroughly mixed. The resulting mixture can be characterized as a primary edible food, and edible oil, and silica which is coating the primary edible food by adherence. Next, the boron-containing substance is added to the blend. The boron-containing substance, being a fine powder, will also adhere to the primary food. This process will ensure maximum consumption of the boron-containing substance and synergist with the edible food, and in turn, will ensure maximum insecticidal activity of the preparation. Finally, the non-white pigment is added to the mixture. Following addition of the pigment, the mixture is thoroughly mixed, and is then ready for use.

The following tables are examples of some of the experimental results described above.

Table I shows test data which illustrates the increased efficacy of the composition of the invention due to the addition of silica gel. Test formula #2, the only formula containing silica gel, resulted in a 3-fold higher insecticidal activity compared to boric acid and a 4.2-fold higher insecticidal activity compared to test formula #1, which was similar to test formula #2 but contained no silica gel.

TABLE I

THE INSECTICIDAL ACTIVITY OF BORIC ACID, AND TWO BAIT PREPARATIONS CONTAINING BORIC ACID WITH AND WITHOUT SILICA GEL.

| Test Formula | Insecticidal Activity[a] (# dead/# exposed) |
|---|---|
| Control (Ground corn only) | 0/80 |
| Boric Acid (by itself) | 14/80 |
| Test Formula #1[b] | 10/80 |
| Test Formula #2[c] | 42/80 |

[a]Insecticidal activity measured at 24 hours post-exposure.
[b]TEST FORMULA: #1
Boric Acid: 55%
Ground corn: 44%
Corn oil 1%
[c]TEST FORMULA: #2
Boric Acid: 55%
Ground corn: 39%
Corn oil: 1%
Sipernat 22S: 5%

Table II shows test data which illustrates the optimum concentrations of edible food in proportion to boric acid. The formulation containing 65.5% edible food with 30% boric acid (1) resulted in 25% mortality within the first 24 hours of the experiment, (2) resulted in the highest efficacy measured at 48 hrs. and (3) was among the most efficacious formulations when insectical activity was measured at 72 hours.

TABLE II

RELATIONSHIP OF BORIC ACID CONCENTRATION TO INSECTICIDAL ACTIVITY IN VARIOUS PREPARATIONS CONTAINING AN EDIBLE FOOD, SILICA, AND AN EDIBLE OIL.

| Bait Composition (Edible food:Boric Acid) | Insecticidal Activity (# dead/# exposed to preparation) Time Post-Exposure (hrs) | | |
|---|---|---|---|
| | 24 | 48 | 72 |
| 100.0:0 | 0/80 | 1/80 | 4/80 |
| 90.5:5[a] | 4/80 | 20/80 | 38/80 |
| 85.5:10[a] | 14/80 | 24/80 | 41/80 |
| 75.5:20[a] | 20/80 | 39/80 | 64/80 |
| 65.5:30[a] | 20/80 | 45/80 | 70/80 |
| 55.5:40[a] | 10/80 | 30/80 | 70/80 |
| 45.5:50[a] | 8/80 | 40/80 | 76/80 |

[a]All experimental preparations contained corn as the primary edible food, 2.0% Sipernat 22S as the source of silica and 2.5% corn oil.

Table III shows test data which illustrates the efficacy of the bait in controlling lesser meal worms, compared to powdered boric acid alone.

TABLE III

COMPARISON OF BORIC ACID POWDER AND BORIC ACID CONTAINING BAIT ON CUMULATIVE MORTALITY OF LESSER MEAL WORMS.

| TREATMENT | MORTALITY (%) TIME POST-EXPOSURE (HRS.) | | | | | | |
|---|---|---|---|---|---|---|---|
| | 24 | 48 | 72 | 96 | 120 | 144 | 168 |
| Control | 0 | 0 | 0 | 0 | 0 | 0 | 0 |
| Boric Acid | 20 | 50 | 58 | 70 | 80 | 86 | 94 |
| Bait | 14 | 62 | 92 | 98 | 100 | 100 | 100 |

What is claimed is:

1. An insecticidal composition comprising a mixture of:
from about 55.5% to about 75.5% by weight of a ground cereal grain;
from about 20% to about 40% by weight of powdered boric acid,
from about 1% to about 5% by weight of an edible oil from the class consisting of corn oil and soy cil, and
from about 1% to about 5% by weight of silica gel.

2. The invention of claim 1, said ground cereal grain being middlings.

3. The invention of claim 1, said ground cereal grain being corn meal.

4. The invention of claim 1, said edible oil being corn oil.

5. The invention of claim 1, said edible oil being soy oil.

6. The invention of claim 1, said ground grain being about 65.5% by weight.

7. The invention of claim 1, said powdered boric acid being about 30% by weight.

8. The invention of claim 1, said edible oil being about 2.5% by weight.

9. The invention of claim 1, said silica gel being about 2% by weight.

10. The invention of claim 1, further comprising from about 0.05% to about 0.2% of a non-white coloring agent.

11. The invention of claim 10, said non-white coloring agent being about 0.1% by weight.

12. The invention of claim 10, said non-white coloring agent comprising a fluorescent pigment.

13. A method for controlling darkling beetles and hide beetles comprising applying in an area inhabited by them or that may be inhabited them an insecticidal composition comprising a mixture of:

from about 55.5% to about 75.5 % by weight of a ground grain from the class of grains consisting of wheat and corn, from about 20% to about 40% by weight of powdered boric acid, from about 1% to about 5% by weight of an edible oil from the class consisting of corn oil and soy oil, and from about 1% to about 5% by weight of silica gel.

14. The invention of claim 13, said insecticidal composition further comprising from about 0.05% to about 0.2% by weight of a non-white coloring agent.

15. A process for manufacturing an insecticidal composition comprising:

mixing from about 55.5% to about 75.5% by weight of a ground grain from the class consisting of grains consisting of wheat and corn, with from about 1% to about 5% by weight of an edible oil from the class consisting of corn oil and soy oil, then admixing from about 1% to about 5% by weight of silica gel, then admixing from about 20% to about 40% by weight of powdered boric acid.

16. The invention of claim 5, then admixing from about 0.05% to about 0.2% by weight of a non-white coloring agent.

* * * * *

UNITED STATES PATENT AND TRADEMARK OFFICE
CERTIFICATE OF CORRECTION

PATENT NO. : 4,996,053

DATED : February 26, 1991

INVENTOR(S) : Richard P. Hatcher

It is certified that error appears in the above-identified patent and that said Letters Patent is hereby corrected as shown below:

On the title page, item [54] line 2, and column 1, line 3, in the title the word "METAL" should read --MEAL--.

Signed and Sealed this

Sixth Day of July, 1993

Attest:

MICHAEL K. KIRK

*Attesting Officer*   Acting Commissioner of Patents and Trademarks